US007181375B2

(12) United States Patent
Rao et al.

(10) Patent No.: US 7,181,375 B2
(45) Date of Patent: Feb. 20, 2007

(54) PATIENT DATA MINING FOR DIAGNOSIS AND PROJECTIONS OF PATIENT STATES

(75) Inventors: R. Bharat Rao, Berwyn, PA (US); Sathyakama Sandilya, Cranbury, NJ (US); Radu Stefan Niculescu, Pittsburgh, PA (US); Arun Kumar Goel, Colonia, NJ (US)

(73) Assignees: Siemens Medical Solutions USA, Inc., Malvern, PA (US); Siemens Corporate Research, Inc., Princeton, NJ (US)

( * ) Notice: Subject to any disclaimer, the term of this patent is extended or adjusted under 35 U.S.C. 154(b) by 899 days.

(21) Appl. No.: 10/287,053

(22) Filed: Nov. 4, 2002

(65) Prior Publication Data

US 2003/0126101 A1 Jul. 3, 2003

Related U.S. Application Data

(60) Provisional application No. 60/335,542, filed on Nov. 2, 2001.

(51) Int. Cl.
G06F 17/10 (2006.01)
(52) U.S. Cl. .............................. 703/2; 705/3; 128/920
(58) Field of Classification Search ............... 703/11, 703/2; 705/3; 128/920; 600/300
See application file for complete search history.

(56) References Cited

U.S. PATENT DOCUMENTS

| 5,657,255 A * | 8/1997 | Fink et al. ............... 703/11 |
| 5,724,573 A | 3/1998 | Agrawal et al. |
| 5,738,102 A | 4/1998 | Lemelson |
| 5,903,889 A | 5/1999 | de la Huerga et al. |
| 5,908,383 A | 6/1999 | Brynjestad |
| 5,924,074 A | 7/1999 | Evans |
| 6,039,688 A | 3/2000 | Douglas et al. |

(Continued)

FOREIGN PATENT DOCUMENTS

DE 198 20 276 11/1999

(Continued)

OTHER PUBLICATIONS

Mitchell T M: "Machine learning and data Mining" Communications of the ACM, Nov. 1999, ACM, USA, 'Online! vol. 42, No. 11, Nov. 1999, pp. 30-36, XP002258895 ISSN: 0001-0782 Retrieved from the Internet: ,URL :http://portal.acm.org/ft-gateway.cfm?=3957717&CFTOKEN=38351001> Retrieved on Oct. 23, 2003! the whole document.

(Continued)

Primary Examiner—Albert W. Paladini

(57) ABSTRACT

A method and system for determining patient states is provided. The method includes the steps of data mining a patient record using a domain knowledge base relating to a disease of interest; inputting the mined data into a model of the disease of interest; and determining a state of the patient based on the model. The system includes a data miner for mining information from a patient record using a domain knowledge base relating to a disease of interest; and a processor for creating a patient model of the disease of interest, processing the mined data in the model to determine a current state of the patient and future states for different courses of treatment, and recommending a therapy based on the determined future state.

41 Claims, 6 Drawing Sheets

U.S. PATENT DOCUMENTS

| | | | |
|---|---|---|---|
| 6,067,466 | A | 5/2000 | Griffith et al. ............... 600/513 |
| 6,125,194 | A | 9/2000 | Yeh et al. |
| 6,139,494 | A | 10/2000 | Cairnes |
| 6,173,280 | B1 | 1/2001 | Ramkumar et al. |
| 6,212,526 | B1 | 4/2001 | Chaudhuri et al. |
| 6,322,504 | B1 | 11/2001 | Kirshner |
| 6,478,737 | B2 | 11/2002 | Bardy |
| 6,484,144 | B2 * | 11/2002 | Martin et al. ................... 705/2 |
| 6,551,266 | B1 * | 4/2003 | Davis, Jr. .................. 604/6.09 |
| 6,611,825 | B1 | 8/2003 | Billheimer et al. |
| 6,641,532 | B2 * | 11/2003 | Iliff ............................ 600/300 |
| 6,754,655 | B1 * | 6/2004 | Segal ............................. 707/6 |
| 6,802,810 | B2 * | 10/2004 | Ciarniello et al. .......... 600/300 |
| 6,961,687 | B1 | 11/2005 | Myers, Jr. et al. |
| 2001/0023419 | A1 | 9/2001 | Desieno et al. |
| 2003/0120133 | A1 | 6/2003 | Rao et al. |
| 2003/0120134 | A1 | 6/2003 | Rao et al. |
| 2003/0120458 | A1 | 6/2003 | Rao et al. |
| 2003/0120514 | A1 | 6/2003 | Rao et al. |
| 2003/0125984 | A1 | 7/2003 | Rao et al. |
| 2003/0125985 | A1 | 7/2003 | Rao et al. |
| 2003/0125988 | A1 | 7/2003 | Rao et al. |
| 2003/0130871 | A1 | 7/2003 | Rao et al. |
| 2003/0135391 | A1 | 7/2003 | Edmundson et al. |
| 2004/0243586 | A1 | 12/2004 | Byers |

FOREIGN PATENT DOCUMENTS

| | | |
|---|---|---|
| EP | 0 596 247 A2 | 5/1994 |
| EP | 0641 863 | 3/1995 |
| GB | 2 332 544 A | 6/1999 |
| WO | WO 98/29790 | 7/1998 |
| WO | WO 00/51054 | 8/2000 |
| WO | WO 00/69331 | 11/2000 |
| WO | WO 01/66007 | 9/2001 |
| WO | WO 01/78005 A2 | 10/2001 |

OTHER PUBLICATIONS

Kleissner C: "Data mining for the enterprise" System Sciences, 1998., Proceedings of the Thirty-First Hawaii International Conference on Kohala Coast, HI, USA Jan. 6-9, 1998, Los Alamitos, CA, USA, IEEE Comput. Soc, US, Jan. 6, 1998, pp. 295-304, XP010262792 ISBN: 0-8186-8255-8 the whole document.

"Improved Diagnostic and Prognostic Assessments Using Health Management Information Fusion", Roemer et al., 20001 IEEE Autotestcon Proceedings, IEEE Systems Readiness Technology Conference, Autotestcon 2001, vol. CONF. 37, Aug. 20, 2001, pp. 365-377.

"Data Mining for Disease Management: Adding Value to Patient Records", Rao et al., Electromedia, Online!, vol. 68, 2000, pp. 63-67, retrieved from the internet: http://www.med.siemens.com/medroot/en/news/electro/issues/pdf/onco_2000_e/9.pdf.

"Information Understanding Integrating Data Fusion and Data Mining Processes", Waltz et al, Circuits and Systems, 1998, ISCAS 98, Proceedings of the 1998 IEEE International Symposium on Monterey, CA, USA May 31-Jun. 3, 1998, NY, NY, USA, IEEE, May 31, 1998, pp. 553-556.

"A Mutually Beneficial Integration of Data Mining and Information Extraction", Nahm et al., Proceedings AAA1, National Conference on Artificial Intelligence, Jul. 30, 2000, pp. 627-632.

"Using Data Mining to Characterize DNA Mutations by Patient Clinical Features", Evans et al., 1997 AMIA Annual Fall Symposium, Proceedings of 1997 AMIA Annual Fall Symposium the Emergence of Internetable Health Care Systems That Really Work, Nashville, TN, pp. 253-257.

"The Colorectal Cancer Recurrence Support (CARES) System", Ong et al., Artificial Intelligence in Medicine, Nov. 1997, Elsevier, Netherlands, vol. 11, No. 3, pp. 175-188.

"Database System Support for Multidimensional Data Analysis in Environmental Epidemiology", Kamp et al., Database Engineering and Applications Symposium, 1997, Ideas 97, Proceedings, International Montreal, Que, Canada, Aug. 25-27, 1997, Los Alamitos, CA, USA, IEEE Comput. Soc., US, pp. 180-188.

Roemer M J et al: "Improved diagnostic and prognostic assessments using health management information fusion" 2001 IEEE Autotestcon Proceedings. IEEE Systems Readiness Technology Conference. Autotestcon 2001. Valley Forge, PA, Aug. 20-23, 2001, IEEE Systems Readiness Technology Conference, New York, NY: IEEE, us, vol. CONF. 37 , Aug. 20, 2001, pp. 365-377, XP010556114 ISBN: 0-7803-7094-5 the whole document.

Rao R. B. et al "Data Mining for Disease Management: Adding Value to Patient Records" Electromedica. 'Online! vol. 68, 2000, pp. 63-67, XP002261087 Retrieved form the Internet: URL:http//www.med.siemens.com/medroot/en/news/electro/issues/pdf/onco_2000_e/9.pdf> retrieved on Nov. 11, 2003! the whole document.

Un Yong Nahm et al: "A Mutually Benficial Integration of Data Mining and Information Extraction" Proceedings AAAI, National Conference on Artificial Intelligence, XX, XX, Jul. 30, 2000, pp. 627-632, XP008002223 the whole document.

Waltz E L: "Information understanding integrating data fusion and data mining processes" Circuits and Systems, 1998, ISCAS '98. Proceedings of the 1998 IEEE International Symposium on Monterey, CA, USA May 31-Jun. 3, 1998, New York, NY, USA, IEEE, US, May 31, 1998, pp. 553-556, XP010289780 ISBN: 0-7803-4455-3 the whole document.

* cited by examiner

PATIENT DATA MINING FOR DIAGNOSIS AND PROJECTIONS OF PATIENT STATES

CROSS REFERENCE TO RELATED APPLICATIONS

This application claims the benefit of U.S. Provisional Application Ser. No. 60/335,542, filed on Nov. 2, 2001, which is incorporated by reference herein in its entirety.

FIELD OF THE INVENTION

The present invention relates to medical information processing systems, and, more particularly to a computerized system and method for diagnosing a current state, or condition, of a patient, projecting a future state of the patient based on various available treatment options, and recommending a course of therapy.

BACKGROUND OF THE INVENTION

The major challenge facing health care providers in the present climate is to achieve a balance between a desire to reduce costs and the overriding need to maintain quality in patient care. The attempt to reduce costs without compromising quality centers around a two-fold effort to eliminate wasteful practices, and to concentrate resources on identifying those patients with the greatest likelihood of poor outcomes. By their very nature, both efforts require the use of accurate and comprehensive databases that can be extracted and analyzed to provide a basis for intervention. Two such areas with potential for intervention are the identification of high-risk patients that would benefit from proactive approaches, e.g., by determining their future states, and the elimination wasteful practices that increase cost without a commensurate improvement in quality, or prolong length of stay, e.g., by accurately diagnosing their current state.

The problem that confronts any such effort, however, is the lack of high-quality data that can be extracted and analyzed in any meaningful or reliable way, since most hospital databases are created in text-based or other non-structured formats. Most hospitals either resort to the use of random sampling to manually review a small proportion of patient charts, or focus on relatively easily available structured information (based, for example, on DRG or ICD-9 codes) to guide their decision-making. Any truly comprehensive changes are thus left to an imperfect process, or must await a prospective data-entry system that has the capability of acting as an adequate repository of all the differing formats in which patient data are stored. At the present time managing all these different formats presents a formidable challenge in even one hospital database, let alone in different systems.

In view of the above, there exists a need for techniques to collect patient information from a variety of sources to quickly and efficiently diagnose a current state or condition of a patient and to project the future state of the patient to help quickly identify high-risk patients, and to determine cost-effective treatments and/or therapies.

SUMMARY OF THE INVENTION

A system and method for determining states or conditions of a patient is provided.

According to one aspect of the present invention, a method for determining patient states is provided including the steps of data mining a patient record using a domain knowledge base relating to a disease of interest; inputting the mined data into a model of the disease of interest; and determining a state of the patient based on the model.

According to another aspect of the present invention, a system for determining patient states includes a data miner for mining information from a patient record using a domain knowledge base relating to a disease of interest; and a processor for creating a patient model of the disease of interest, processing the mined data in the model to determine a current state of the patient and future states for different courses of treatment and recommending a therapy based on the estimated future disease states.

BRIEF DESCRIPTION OF THE DRAWINGS

The above and other aspects, features and advantages of the present invention will become more apparent from the following detailed description when taken in conjunction with the accompanying drawings in which.

DESCRIPTION OF PREFERRED EMBODIMENTS

To facilitate a clear understanding of the present invention, illustrative examples are provided herein which describe certain aspects of the invention. However, it is to be appreciated that these illustrations are not meant to limit the scope of the invention, and are provided herein to illustrate certain concepts associated with the invention.

A system and method for determining states or conditions of a patient is provided. By data mining information from various sources, e.g., structured and unstructured, the present invention can gather all the information available in a patient record and use this gathered information to make a probabilistic assertions concerning prior states and a current state of a particular patient. The prior and current states of the patient can then be used in a patient model to determine future states of the patient.

It is to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device.

It is to be understood that, because some of the constituent system components and method steps depicted in the accompanying figures are preferably implemented in software, the actual connections between the system components (or the process steps) may differ depending upon the manner in which the present invention is programmed.

Figure 1:
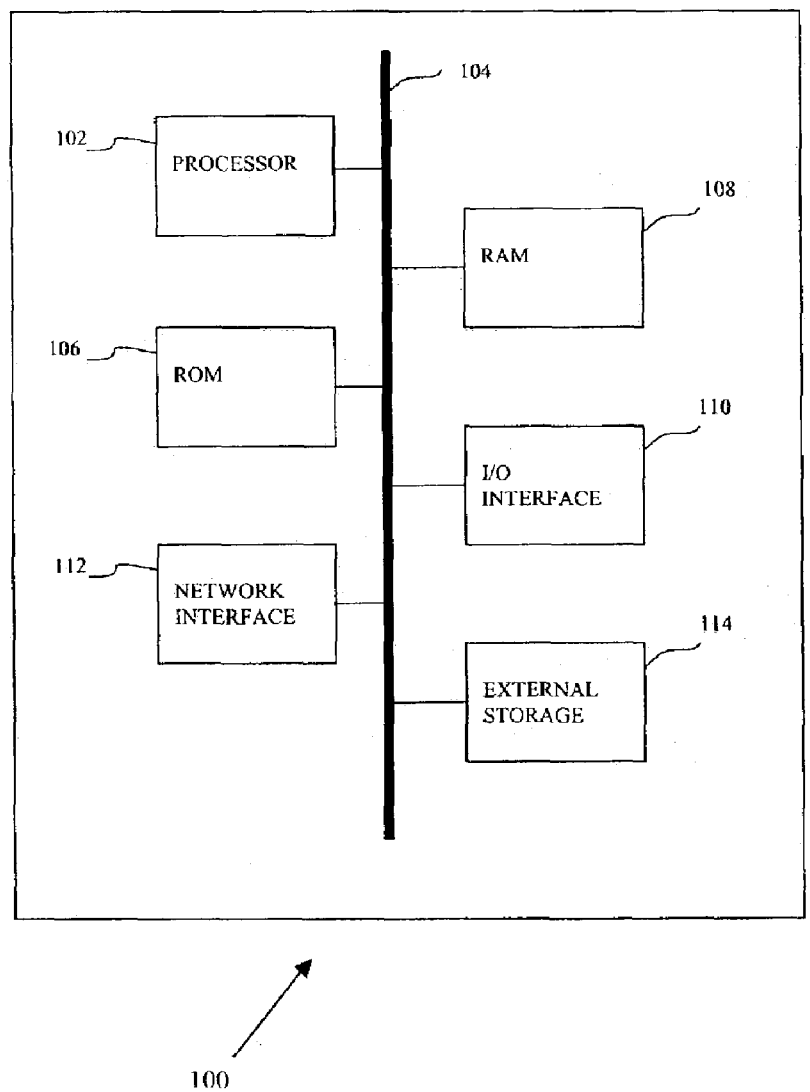
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read-only memory (ROM) 106, a random access memory (RAM) 108, an I/O interface 110, a network interface 112, and external storage 114 are operatively coupled to the system bus 104. Various peripheral devices such as, for example, a display device, a disk storage device (e.g., a magnetic or optical disk storage device), a keyboard, and a mouse, may be operatively coupled to the system bus 104 by the I/O interface 110 or the network interface 112.

The computer system 100 may be a standalone system or be linked to a network via the network interface 112. The network interface 112 may be a hard-wired interface. However, in various exemplary embodiments, the network interface 112 can include any device suitable to transmit information to and from another device, such as a universal asynchronous receiver/transmitter (UART), a parallel digital interface, a software interface or any combination of known or later developed software and hardware. The network interface may be linked to various types of networks, including a local area network (LAN), a wide area network (WAN), an intranet, a virtual private network (VPN), and the Internet.

The external storage 114 may be implemented using a database management system (DBMS) managed by the processor 102 and residing on a memory such as a hard disk. However, it should be appreciated that the external storage 114 may be implemented on one or more additional computer systems. For example, the external storage 114 may include a data warehouse system residing on a separate computer system.

Those skilled in the art will appreciate that other alternative computing environments may be used without departing from the spirit and scope of the present invention.

Figure 2:
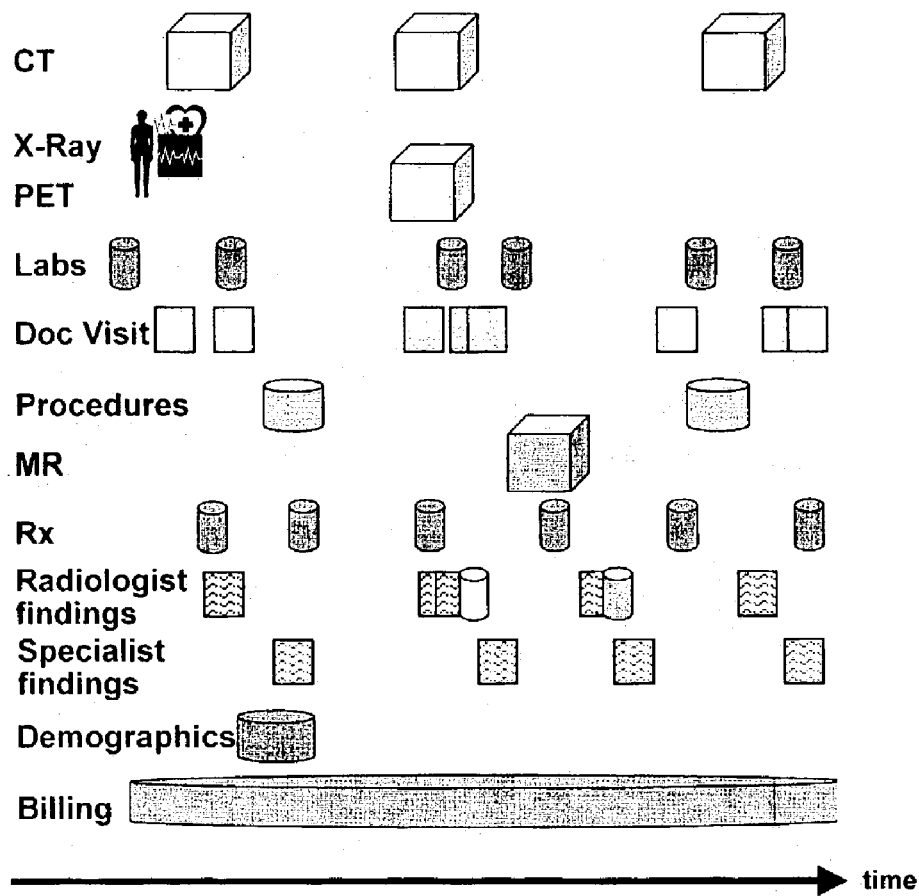
FIG. 2 illustrates an exemplary computerized patient record (CPR)

Increasingly, health care providers are employing automated techniques for information storage and retrieval. The use of a computerized patient record (CPR) to maintain patient information is one such example. As shown in FIG. 2, an exemplary CPR (200) includes information that is collected over the course of a patient's treatment. This information may include, for example, computed tomography (CT) images, X-ray images, laboratory test results, doctor progress notes, details about medical procedures, prescription drug information, radiological reports, other specialist reports, demographic information, and billing (financial) information.

A CPR typically draws from a plurality of data sources, each of which typically reflects a different aspect of a patient's care. Structured data sources, such as financial, laboratory, and pharmacy databases, generally maintain patient information in database tables. Information may also be stored in unstructured data sources, such as, for example, free text, images, and waveforms. Often, key clinical findings are only stored within physician reports, e.g., dictations.

Figure 3:
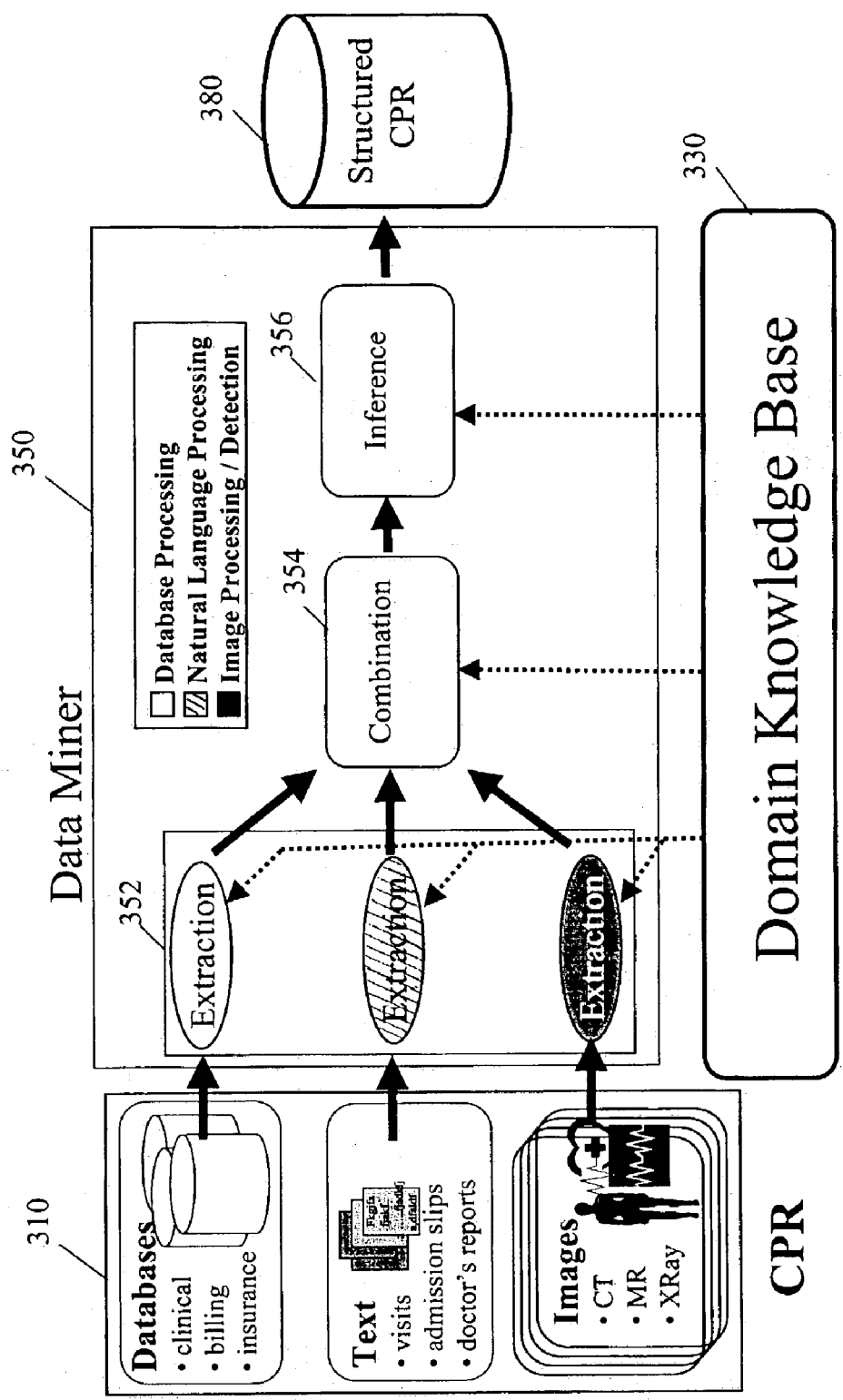
FIG. 3 illustrates an exemplary data mining framework for mining high-quality structured medical information.

FIG. 3 illustrates an exemplary data mining system for mining high-quality structured clinical information using data mining techniques described in "Patient Data Mining," by Rao et al., copending U.S. patent application Ser. No. 10/287,055, filed herewith, which is incorporated by reference in its entirety. The data mining system includes a data miner (350) that mines information from a CPR (310) using domain-specific knowledge contained in a knowledge base (330). The data miner (350) includes components for extracting information from the CPR (352), combining all available evidence in a principled fashion over time (354), and drawing inferences from this combination process (356). The mined information may be stored in a structured CPR database (380). In this manner, all information contained in a CPR, whether from a structured or unstructured source, will be stored in a structured fashion.

The extraction component (352) deals with gleaning small pieces of information from each data source regarding a patient, which are represented as probabilistic assertions about the patient at a particular time. These probabilistic assertions are called elements. The combination component (354) combines all the elements that refer to the same variable at the same time period to form one unified probabilistic assertion regarding that variable. These unified probabilistic assertions are called factoids. The inference component (356) deals with the combination of these factoids, at the same point in time and/or at different points in time, to produce a coherent and concise picture of the progression of the patient's state over time. This progression of the patient's state is called a state sequence.

The present invention can build an individual model of the state of a patient. The patient state is simply a collection of variables that one may care about relating to the patient. The information of interest may include a state sequence, i.e., the value of the patient state at different points in time during the patient's treatment.

Each of the above components uses detailed knowledge regarding the domain of interest, such as, for example, a disease of interest. This domain knowledge base (330) can come in two forms. It can be encoded as an input to the system, or as programs that produce information that can be understood by the system. The part of the domain knowledge base (330) that is input to the present form of the system may also be learned from data.

As mentioned, the extraction component (352) takes information from the CPR (310) to produce probabilistic assertions (elements) about the patient that are relevant to an instant in time or time period. This process is carried out with the guidance of the domain knowledge that is contained in the domain knowledge base (330). The domain knowledge required for extraction is generally specific to each source.

Figure 4:
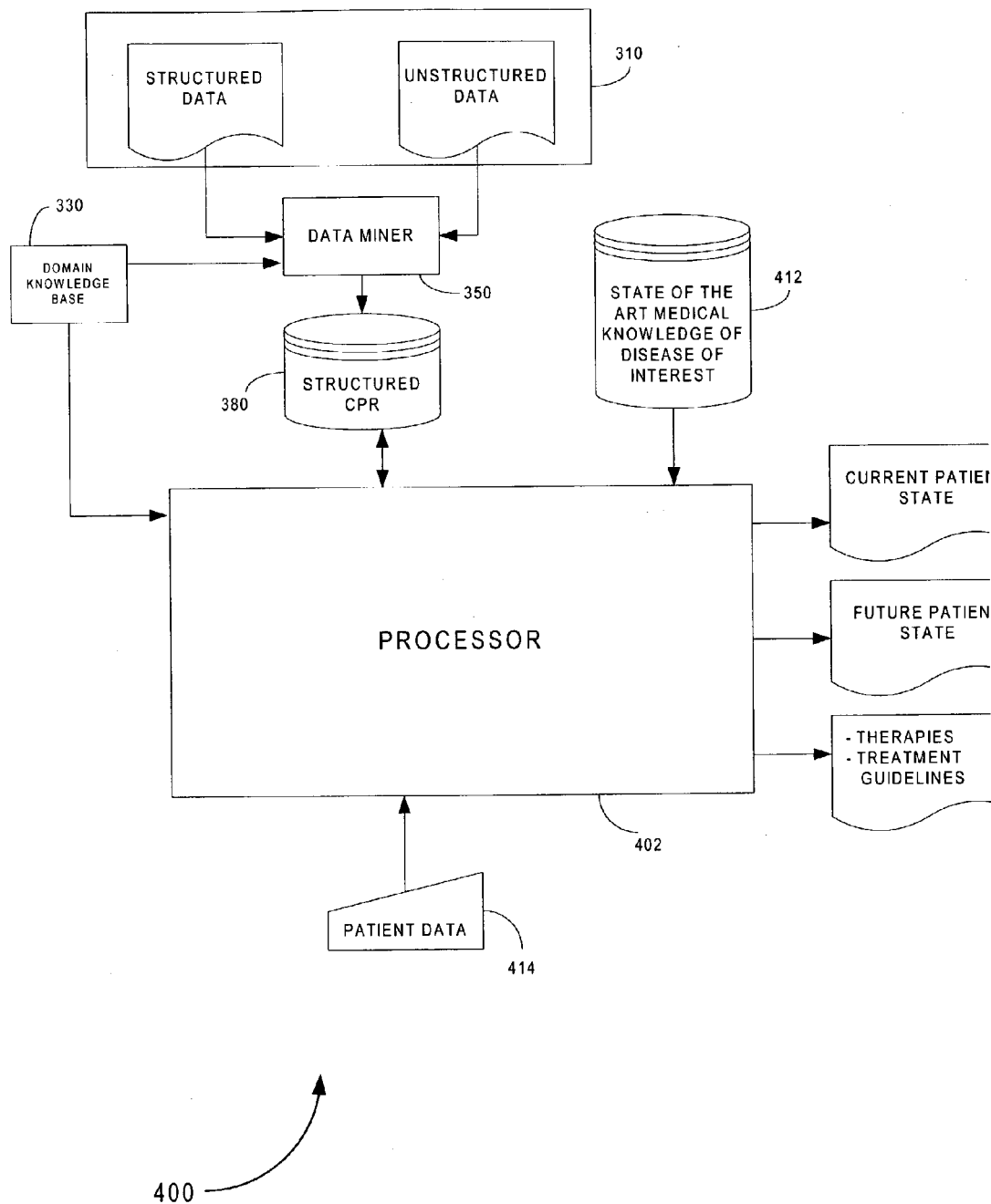
FIG. 4 illustrates a block diagram of an exemplary diagnosis and projection system according to an embodiment of the present invention.

Referring to FIG. 4, an exemplary diagnosis and projection system 400 according to an embodiment of the present invention is illustrated. The system 400 includes a processor 402 for extracting information from the structured CPR database 380, for creating models of diseases of interest and for processing the extracted information in a model to project a future state of a patient.

The processor is further coupled to a second database 412 including "state of the art" information relating to a disease of interest. This information may include standard procedures, established guidelines for treatments, standardized tests for assessment, etc. Additionally, the processor 402 is adapted to receive manually inputted patient data 414 which it may process and store in the structured database 380.

Each task performed by the system 400 is performed by an executable module residing either in the processor of the system 402 and/or in a memory device (e.g., RAM, ROM, external storage, etc.) of the system.

Figure 5:
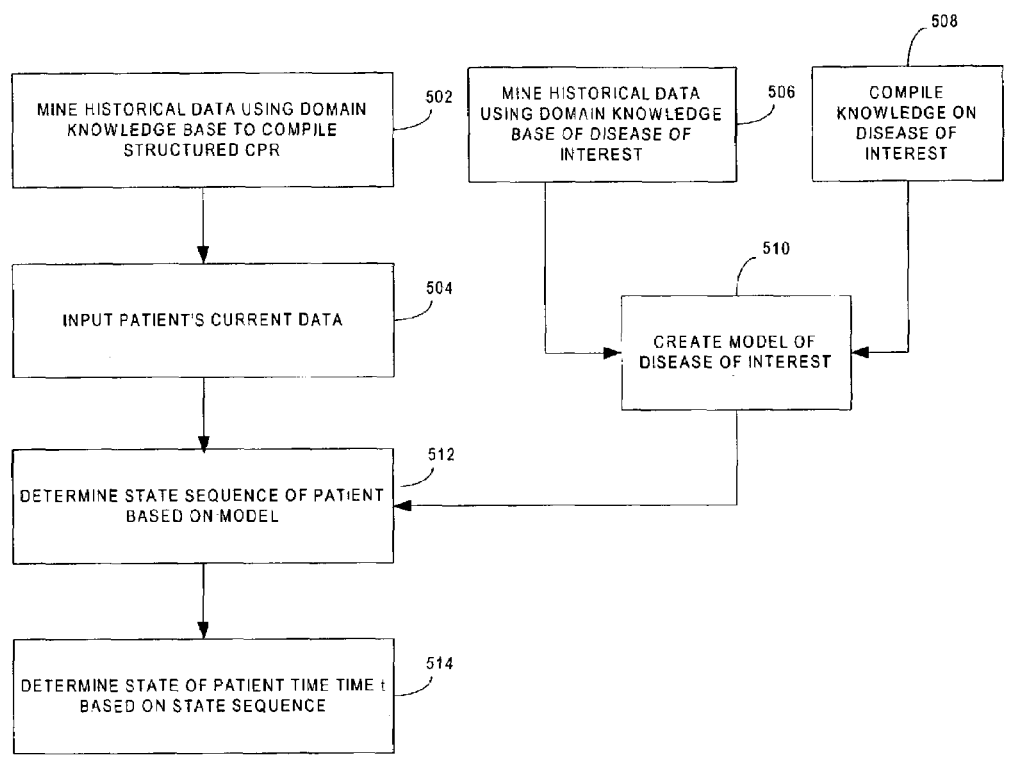
FIG. 5 illustrates a flow diagram for diagnosing and projecting patient states according to an embodiment of the present invention.

Referring to FIGS. 4 and 5, the diagnosis and projection system will be further described along with methods for diagnosing a patient's current state, for creating patient models based on a disease of interest, and for projecting a future state of a patient based on the patient's current state and the model.

First, a patient record 310 is assembled during the course of treatment of a patient over time. Additionally, a plurality of patient records for different patients (i.e., population-based data) may be assembled for a particular hospital and stored in common data storage area as the individual patient record 310. This historical data is mined using a domain knowledge base relating to a disease of interest and compiled in a structured CPR database 380 (step 502). The patient's current data is inputted into the system either manually 414 or by mining data from current tests (step 504).

A model is created to simulate a patient with similar characteristics of the patient being diagnosed. The processor 402 generates data for the model by mining data of similar patients from population-based data sources via data miner 350 using a domain knowledge base 330 of the disease of interest (step 506). The processor 402 will then create the model of the disease of interest based on the mined data (step 510). Additionally, the processor may compile knowledge on the disease of interest from the second medical knowledge database 412 (step 508) and refine the model with this knowledge.

Once the patient model is created, all available patient data, i.e., data mined from structured and unstructured sources and/or manually input, will be entered into the model and various simulations will be run. The processor will determine a state sequence over time for the patient based on the model (step 512). The processor can further determine a future state at a particular time t, from the state sequence, to determine a preferred treatment guideline for the patient (step 514).

The development of the method according to a preferred embodiment of the present invention will now be described below in detail.

Let S be a continuous time random process taking values in $\Sigma$ that represents the state of the system. Let $T=\{t_1, t_2, \ldots, t_n\}$, where $t_i<t_{i+1}$, be the n "times of interest" when S has to be inferred. Let $S_i$ refer to the sample of S at time $t_i \epsilon T$. Let V be the set of variables that depend upon S. Let O be set of all (probabilistic) observations for all variables, $v \epsilon V$. Let $O_i$ be the set of all observations "assigned" to $t_i \epsilon T$; i.e., all observations about variables, $v \epsilon V$, that are relevant for this time-step ti. Similarly, let $O^j_i(v)$ be the j-th observation for variable v assigned to $t_i$. Let seq=$<S_1, S_2, \ldots S_n>$ be a random variable in $\Sigma^n$; i.e., each realization of seq is a state sequence across T. GOAL: Estimate the most likely state sequence, $seq_{MAP}$, (the maximum a posteriori (MAP) estimate of seq) given O:

$$seq_{MAP} = arg\ max_{seq} P[seq|O]$$

The primary focus of our interest is estimating what happened to the patient across T, the duration of interest. The estimation of the MAP state sequence can be done in two steps, the first of which is combination of observations at a fixed point in time and the second is the propagation of these inferences across time.

Each (smoothed) $O_i$ is in the form of an a posteriori probability of a variable given the small context that it is extracted from. All observations, $O^j_i(v)$, about a variable for a single time $t_i$ are combined into one assertion in a straightforward manner by using Bayes' theorem:

$$P[v_i | O^1_i(v_i), \ldots, O^k_i(v_i)] \propto P[v_i] \cdot \prod_{j=1}^{k} P[O^j_i(v_i) | v_i] \propto \frac{\prod_{j=1}^{k} P[v_i | O^j_i(v_i)]}{P[v_i]^{k-1}}$$

At every $t_i \epsilon T$, the relationships among $S_i$ and V are modeled using a Bayesian Network. Because the state process is modeled as being Markov and the state as being causative (directly or indirectly) of all the variables that we observe, we have the following equation:

$$P[seq | O] \propto P[S_0] \cdot \prod_{i=2}^{n} P[S_i | S_{i-1}] \cdot \prod_{i=1}^{n} P[O_i | S_i] \propto$$

$$\prod_{i=2}^{n} \frac{P[S_i | S_{i-1}]}{P[S_i]} \cdot \prod_{i=1}^{n} P[S_i | O_i]$$

This equation connects the a posteriori probability of seq (any sequence of samples of the state process across time) given all observations, to $P(S_i|O_i)$, the temporally local a posteriori probability of the state given the observations for each time instant. Essentially, we string together the temporally local Bayesian Networks by modeling each state sample, $S_i$, as the cause of the next sample, $S_{i+1}$.

The diagnosis problem is that of estimating the patient's disease state at time $t_n$ as follows:

$$P[S_n|O] = \Sigma P[seq|O]$$

where the summation runs over those sequences seq where the final state is equal to $S_n$.

Further, the method will estimate (prognosing) the patient state (or any other patient variable) at a future time $t_f$. The following expressions are derived from the above equations to perform the prognosis for the patient:

$$P[S_f|O] = \Sigma P[S_f|S_n] P[S_n|O]$$

where $S_f$ is a future state of the patient, and $$P[V_f|O] = \Sigma P[V_f|S_f] P[S_f|S_n] P[S_n|O]$$

Where $V_f$ is a future variable of the patent.

Furthermore, the method can also be used to predict the outcome of various treatment options that the patient may undergo using the same model for the patient's disease state and other variables of interest (which include the relationships between the treatment options and the outcomes thereof). The method determines $P[S_f|O,T_i]$ for each therapy option $T_i$ and then presents this information to physicians so that they may make more informed decisions regarding the future treatment of the patient.

Figure 6:
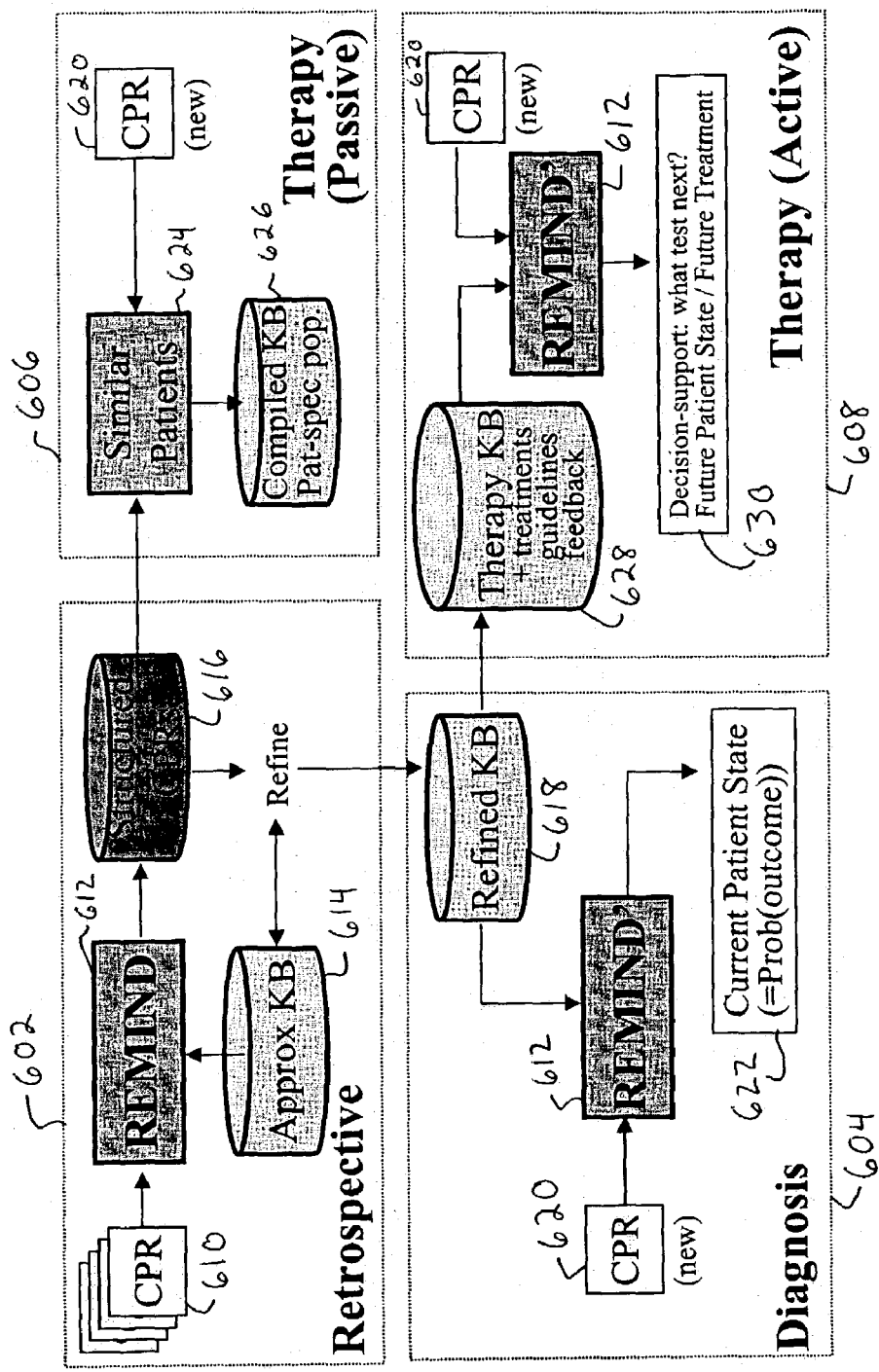
FIG. 6 is a work flow diagram for diagnosing a current patient state, projecting a future patient state and suggesting therapies and treatment based on the patient states.

FIG. 6 is a work flow diagram for diagnosing a current patient state, projecting a future patient state and suggesting therapies and treatment based on the patient states.

First, a retrospective analysis 602 of a plurality of CPRs 610 is conducted via the data miner 612, which is also referred to as a REMIND (Reliable Extraction and Meaningful Inference from Non-structured data) system. The data miner 612 uses an approximate knowledge base 614 to compile structured CPRs 616. The structured CPRs 616 are used to refine the approximate knowledge base 614 to compile a refined knowledge base 618 to be used in a diagnosis phase 604.

In the diagnosis phase 604, the data miner 612 (i.e., the REMIND system) uses the refined knowledge base 618 to interact with a specific individual's CPR 620 to determine the individual's current state 622 as described above. In addition, the system may be configured to determine based on the patient's symptoms, a disease that the patient is at risk for, and present to the physician all the information in the patient record that is relevant to the above disease. For example, if a patient comes in to the emergency room with a chest pain, the system will recognize that the patient is likely to have an acute myocardial infarction (heart attack) and present to the doctor, any information that is available regarding the patients troponin level, ECG reports etc.

Once the retrospective analysis and diagnosis phases are complete, the system and method of the present invention can recommend therapies either passively 606 or actively 608. In the passive therapy phase 606, the system will extract CPRs of similar patients 624 to compile a knowledge base 626 of patient-specific populations to determine patterns of treatments and outcomes of the similar patients. The system will assign an outcome to the future state by finding a patient similar to the patient. The system will assign probabilities to the future states by averaging outcomes of weighted outcomes of the similar patients. This knowledge base 626 will then be used to suggest treatments and therapies to the individual patient based on the most favorable outcomes.

Alternatively, therapies will be actively determined by varying potential future treatments and, in turn, projecting future patient states from the future treatments 630. The data miner 612 will use the information from the individual patient record 620 to run various simulations with a therapy knowledge 628, which is learned from the structured database 616, therapy domain knowledge plus active feedback. Basically, the system evaluates a number of possible future treatment options (one of which is "do nothing") and projects the disease state into the future, e.g., if we put the patient on Drug 1 then what will happen".

Then, the system evaluates each of these treatments by looking at the future state of the patient. Simply, if using Drug 1 he dies with a probability of 95% but with Drug 2 he dies with a probability of 10%, the system will suggest Drug 2. The system will also consider other issues, like cost. If Drug 1 determines P (poor outcome)=84% and "Do nothing" (treatment 2) is P (poor outcome)=85%, and Drug 1 costs $5,000,000, the system might recommend against giving Drug 1. Similarly, the system will look at quality of life metrics, where if Drug 1 has severe side effects and only improves survival by 1%, it will not be recommended, or a combination of outcome, costs, quality of life, and other measures can be used to pick the best treatment.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for determining patient states, the method comprising:
    data mining a patient record using a domain knowledge base relating to a disease of interest, the data mining including mining unstructured data of the patient record;
    inputting the mined data into a model of the disease of interest; and
    determining a state of the patient based on the model.

2. The method as in claim 1, wherein the state is assigned a probability.

3. The method as in claim 1, further comprising determining a sequence of states of the patient.

4. The method as in claim 3, wherein the sequence is assigned a probability.

5. The method as in claim 1, further comprising determining a future state of the patient.

6. The method as in claim 5, wherein the future state is assigned a probability.

7. The method as in claim 1, further comprising creating the model of the disease of interest by mining population-based data using the domain knowledge of the disease of interest.

8. The method as in claim 1, further comprising determining a variable of the patient state.

9. The method as in claim 8, wherein the variable is assigned a probability.

10. A system for determining patient states, the system comprising:
    a data miner for mining information from a patient record using a domain knowledge base relating to a disease of interest, the data mining including mining unstructured data of the patient record; and
    a processor for creating a patient model of the disease of interest and processing the mined data in the model to determine a state of the patient.

11. The system as in claim 10, wherein the processor assigns a probability to the patient state.

12. The system as in claim 10, wherein the processor determines a sequence of states of the patient.

13. The system as in claim 12, wherein the processor assigns a probability to the sequence.

14. The system as in claim 10, wherein the processor determines a future state of the patient.

15. The system as in claim 14, wherein the processor assigns a probability to the future state.

16. The system as in claim 10, wherein the data miner mines population-based data using the domain knowledge of the disease of interest and the processor creates the model of the disease of interest from the population-based mined data.

17. The system as in claim 14, wherein the processor assigns an outcome to the future state by finding a patient similar to the patient.

18. The system as in claim 14, wherein the processor determines a plurality of similar patients, and assigns probabilities to future states by averaging outcomes of the similar patients.

19. The system as in claim 18, wherein the processor assigns weights to the outcomes of plurality of similar patients.

20. The system as in claim 10, wherein the processor determines a variable related to the patient state.

21. The system as in claim 20, wherein the variable is assigned a probability.

22. The system as in claim 14, wherein the processor determines a plurality of outcomes by simulating a plurality of treatments based on the mined data of the patient.

23. The system as in claim 22, wherein the processor assigns probabilities to the outcomes and suggests a therapy.

24. A program storage device readable by a machine, tangibly embodying a program of instructions executable by the machine to perform a method for determining patient states, the method comprising:
   data mining unstructured data of a patient record using a domain knowledge base relating to a disease of interest;
   inputting the mined data into a model of the disease of interest; and
   determining a state of the patient based on the model.

25. A method for determining patient states, the method comprising:
   data mining a patient record using a domain knowledge base relating to a disease of interest;
   inputting the mined data into a model of the disease of interest;
   determining a state of the patient based on the model; and
   assigning a probability of existence of the state.

26. The method as in claim 25 further comprising determining a sequence of states of the patient, wherein the probability is assigned to the sequence.

27. The method as in claim 25 further comprising determining a future state of the patient, wherein another probability is assigned to the future state.

28. The method as in claim 25 further comprising determining a variable of the patient state, wherein the variable is assigned another probability.

29. A system for determining patient states, the system comprising:
   a data miner for mining information from a patient record using a domain knowledge base relating to a disease of interest; and
   a processor for creating a patient model of the disease of interest, processing the mined data in the model to determine a state of the patient and assigning a probability of existence of the state.

30. The system as in claim 29 wherein the processor is operable to determine a sequence of states of the patient and operable to assign another probability to the sequence.

31. The system as in claim 29 wherein the processor is operable to determine a future state of the patient and operable to assign another probability to the future state.

32. The system as in claim 29 wherein the processor is operable to determine a variable related to the patient state and operable to assign another probability to the variable.

33. The system as in claim 29 wherein the processor is operable to determine a plurality of outcomes by simulating a plurality of treatments based on the mined data of the patient and is operable to assign probabilities to the outcomes.

34. A method for determining patient states, the method comprising:
   data mining a patient record using a domain knowledge base relating to a disease of interest;
   inputting the mined data into a model of the disease of interest; and
   determining a future state of the patient based on the model;
   wherein the mining comprises mining unstructured data, a probability of existence is assigned to the future state or combinations thereof.

35. The method of claim 34 wherein the mining comprises mining unstructured data.

36. The method of claim 34 wherein the probability is assigned to the future state.

37. A system for determining patent states, the system comprising:
   a data miner for mining information from a patient record using a domain knowledge base relating to a disease of interest; and
   a processor for creating a patient model of the disease of interest and processing the mined data in the model to determine a state of the patient;
   wherein the mining comprises mining unstructured data, a probability of existence is assigned to the future state or combinations thereof.

38. The system of claim 37 wherein the mining comprises mining unstructured data.

39. The system of claim 37 wherein the probability is assigned to the future state.

40. The method of claim 1 further comprising:
   inferring a factoid from a plurality of data output by the data mining;
   wherein inputting comprises inputting the factoid.

41. The method of claim 25 wherein determining the state and assigning the probability comprise determining a posteriori probability as a function observations from the mined data.

* * * * *